(12) United States Patent
Kyd et al.

(10) Patent No.: US 6,245,338 B1
(45) Date of Patent: Jun. 12, 2001

(54) **OMP26 ANTIGEN FROM *HAEMOPHILUS INFLUENZAE***

(75) Inventors: Jennelle Kyd, McKeller; Allan Cripps, Curtin, both of (AU); Christopher John Smith, Dembighshire (GB)

(73) Assignee: Provalis UK Limited (GB)

( * ) Notice: Subject to any disclaimer, the term of this patent is extended or adjusted under 35 U.S.C. 154(b) by 0 days.

(21) Appl. No.: 08/996,408

(22) Filed: Dec. 22, 1997

Related U.S. Application Data (63) Continuation of application No. PCT/GB96/01549, filed on Jun. 27, 1996.

(30) Foreign Application Priority Data

Jun. 27, 1995 (GB) .................................................. 9513074

(51) Int. Cl.⁷ ................................................. A61K 39/102
(52) U.S. Cl. .................................... 424/256.1; 424/185.1; 424/190.1; 424/192.1; 530/350; 435/975
(58) Field of Search ............................. 424/256.1, 185.1, 424/190.1, 192.1; 530/350; 435/975

(56) References Cited

U.S. PATENT DOCUMENTS 5,780,601 * 7/1998 Green et al. .......................... 530/412

FOREIGN PATENT DOCUMENTS

WO 94/12641 6/1994 (WO) .

OTHER PUBLICATIONS

Sirakova et al., Infec. and Immun., 62(5):2002–2020.
Van Alphen, et al., J. Bacteriol., 155(2):878–885.
Chanyangam et al. Infect. Immun. Feb. 1991. 59(2):600–608.*
Cruse et al. The Illustrated Dictionary of Immunology. New York. CRC Press. p. 24, 1995.*
Aasland et al.,1988, J. Bacteriol., 170(12):5916–5918, "Identity of the 17–Kilodalton Protein, a DNA–Binding Protein from *Escherichia coli*, and the firA Gene Product".
Dicker et al., 1991, J. Bacteriol, 173:334–344, "Cloning and nucleotide sequence of the firA gene and the firA200(TS) allel for *E. coli*".
El–Adhami et al., 1999, Infec. and Immun., 67(4):1935–1942, "Characterization of the Gene Encoding a 26–Kilodalton Protein (OMP26) from Nontypeable *Haemophilus influenzae* and Immune Responses to the Recombinant Protein".
Fujita et al., 1989, J. Bacteriol., 1989, 173(3):1333–1339, "The ompH gene of *Yersinia enteroliticea* cloning, sequencing, expression and compurance with known enterobacteria ompH sequences".
Hirvas et al., 1990, FEBS 08227, 262(1):123–126, "Bacterial 'histone–like protein I' (HLP–I) is an outer membrane constituent?".
Hirvas et al., 1991, (173(3):1223–1229, "The ompH Gene of *Yersinia enterocolitica*: Cloning, Sequencing, Expression, and Comparison with Known Enterobacterial ompH Sequences".
Holck et al., 1988, Gene, 67:117–124, "Cloning and sequencing of the gene for the DNA–binding 17K protein of *Escherichia coli*".
Kelly et al., 1993, .Biol. Chem., 268(26):19866–19874, "The firA Gene of *Escherichia coli* encodes UDP–3–0–(R–3–hydroxymyristoyl)–glucosamine N–Acyltransferase".
Koski et al., 1989, J. Biol. Chem., 264(32):18973–18980, "Isolation, Cloning, and Primary Structure of a Cationic 16–kDa Outer Membrane Protein of *Salmonella typhimurium*".
Koski et al., 1990, Gene, 88:117–120, "Complete sequence of the ompH gene encoding the 16–kDa cationic outer membrane protein of *Salmonella typhimurium*".
Kyd et al., 2000, J. Biotechnol., 83:85–90, "Identifying vaccine antigens and assessing delivery systems for the prevention of bacterial infections".
Kyd et al., 1999, J. Biotechnol., 73:103–108, "Nontypeable *Haemophilus influenzae*: challenges in developing a vaccine".
Kyd et al., 1999, Clin. Infec. Dis., 28:238, "Towards a Protein Vaccine for Neotypeable *Haemophilus influenzae*".
Kyd et al., 1998, Infec. Immun., 66:2272–2278, "Potential of a novel protein, OMP26, from nontypeable *Haemophilus influenzae* to enhance pulmonary clearance in a rat model".
Kyd et al., 1996, Vaccine, 14(15):1471–1478, "Modulation of antigen–specific T and B cell responses influence bacterial clearance of non–typeable *Haemophilus influenzae* from the lung in a rat model".
Kyd et al., 1995, Infec. and Immun., 63(8):2931–2940, "Enhanced Respiratory Clearance of Nontypeable *Haemophilus influenzae* following Mucosal Immunization with P6 in a Rat Model".
Manoha et al., 1994, Biochemie, 76:9–14, "Cloning and expression of two *Pasteurella multocida* genes in *Escherichia coli*".
Webb et al., Protein Expression and Purification, 1999, 15:1–7, "A Method for the Purification and Refolding of a Recombinant Form of the Nontypeabale *Haemophilus influenzae* P5 Outer Membrane Protein Fused to Polyhistidine".
Coulton et al., Can. J. Microbiol. 29:280–87 (1983).
Kyd et al., Infec. and Immun., 62(12):5652–5658.
Fleischmann et al., Science, 269:496–512.

* cited by examiner

Primary Examiner—Jennifer Graser
(74) Attorney, Agent, or Firm—Pennie & Edmonds LLP (57) ABSTRACT

A novel antigenic protein derived from the outer membrane of *H. influenzae* is provided. DNA sequences encoding such a protein are also provided as are vaccines comprising the protein and methods of immunizing a subject against *H. influenzae* infection. The invention also includes methods for the prophylaxis or treatment of respiratory tract infections or otitis media, as well as methods for the detection of *H. influenzae*, and kits for use in such methods.

31 Claims, 7 Drawing Sheets

|  | 10 | 20 | 30 | 40 | 50 |  |
|---|---|---|---|---|---|---|
|  | 1234567890 | 1234567890 | 1234567890 | 1234567890 | 1234567890 |  |
|  | ATGAAAAACA | TCGCAAAAGT | AACCGCACTT | GCTTTAGGTA | TTGCACTTGC | 50 |
|  | M K N I | A K V | T A L | A L G I | A L A |  |
|  | TTCAGGCTAT | GCTTCCGCTG | AAGAAAAAAT | TGCTTTCATT | AATGCAGGTT | 100 |
|  | S G Y | A S A E | E K I | A F I | N A G Y |  |
|  | ATATTTTTCA | ACATCACCCA | GATCGCCAAG | CGGTAGCAGA | TAAACTTGAT | 150 |
|  | I F Q | H H P | D R Q A | V A D | K L D |  |
|  | GCTGAATTTA | AACCTGTAGC | TGAGAAATTA | GCAGCAAGCA | AAAAGAAGT | 200 |
|  | A E F K | P V A | E K L | A A S K | K E V |  |
|  | TGATGATAAA | ATTGCTGCTG | CTCGTAAAAA | AGTAGAAGCA | AAAGTTGCGG | 250 |
|  | D D K | I A A A | R K K | V E A | K V A A |  |
|  | CTTTAGAAAA | AGATGCACCT | CGCTTACGTC | AAGCTGATAT | TCAAAAACGC | 300 |
|  | L E K | D A P | R L R Q | A D I | Q K R |  |
|  | CAAGAAGAAA | TTAATAAATT | AGGTGCGGCT | GAAGATGCTG | AATTACAAAA | 350 |
|  | Q E E I | N K L | G A A | E D A E | L Q K |  |
|  | ATTAATGCAA | GAACAAGATA | AAAAAGTTCA | AGAATTCCAA | GCTCAAAATG | 400 |
|  | L M Q | E Q D K | K V Q | E F Q | A Q N E |  |
|  | AAAAACGTCA | AGCTGAAGAA | CGTGGTAAAT | TATTAGATAG | CATTCAAACT | 450 |
|  | K R Q | A E E | R G K L | L D S | I Q T |  |
|  | GCGACAAATA | ATTTAGCAAG | AGCAAAAGGT | TATACTTATG | TGCTTGATGC | 500 |
|  | A T N N | L A R | A K G | Y T Y V | L D A |  |
|  | AAATTCAGTT | GTATTTGCGG | TAGAGGGTAA | AGATATTACT | GAAGAAGTAT | 550 |
|  | N S V | V F A V | E G K | D I T | E E V L |  |
|  | TAAAATCTAT | CCCTGCTTCT | GAAAAAGCAC | AAGAGAAAAA | ATAATAGGTT | 600 |
|  | K S I | P A S | E K A Q | E K K | X X V |  |
|  | C |  |  |  |  | 601 |

| 1 | 2 | 3 | 4 | 5 | 6 | 7 | 8 | 9 | 10 | 11 | 12 | 13 |
|---|---|---|---|---|---|---|---|---|----|----|----|----|
| Glu | Glu | Lys | Ile | Ala | Phe | Ile | Asn | Ala | Gly | Tyr | Ile | Phe |
| E | E | K | I | A | F | I | N | A | G | Y | I | F |

| 14 | 15 | 16 | 17 | 18 | 19 | 20 | 21 | 22 | 23 | 24 | 25 |
|----|----|----|----|----|----|----|----|----|----|----|----|
| Gln | His | His | Pro | Asp | Arg | - | Ala | Val | - | - | Lys? |
| Q | H | H | P | D | R | - | A | V | - | - | K |

B.

OMP26

*P. muisocida* skp protein            AMATE

*Y. pseudotuberculosis* OMPH

OMP26 ANTIGEN FROM *HAEMOPHILUS INFLUENZAE*

This application is a continuation of PCT/GB96/01549 filed Jun. 27, 1996.

The present invention relates to a novel antigen of *Haemophilus influenzae*, vaccines comprising it and its use in therapy and diagnosis.

*H. influenzae* is a Gram-negative aerobic heterotrophic bacteria with the form of rods (Krieg and Holt (ed), *Bergey's Manual of Systemic Bacteriology*, pp 563 (1984). It is a pathogen in acute respiratory infections and is also found in patients with chronic bronchitis and otitis media.

We have now identified, and purified, a unique 26 kDa outer membrane protein (called OMP26) from NTHI, and have surprisingly found that this protein can, when used as an immunogen, induce protective immune responses against infection with homologous and heterologous strains of NTHi. This protein has a molecular mass on SDS-PAGE similar to P5, but has been found to be distinctly different from the protein.

The outer membrane protein P5 is one of two lower molecular mass bands on SDS-PAGE gels used to subtype *H. influenzae* strains, and has an apparent molecular mass of 25–27 kDa. The P5 protein is heat-modifiable, demonstrating an apparent mass of 35 kDa after heating for 30 min at 100° C. in the presence of β-mercaptoethanol. Recently, another protein expressed by NTHi, called a fimbrin protein, has been characterised and shown to have similar molecular mass properties, heat modifiability and a 92% sequence homology to the previously described P5. The protein, OMP26, does not demonstrate either sequence homology or heat-modifiable characteristics as defined for either P5 or the fimbrin protein.

Thus, in a first aspect, the present invention provides a protein having a molecular weight of 26 kDa, as determined by SDS-PAGE, which protein is an outer membrane protein of *H. influenzae*. This protein is designated OMP26.

Figure 1:
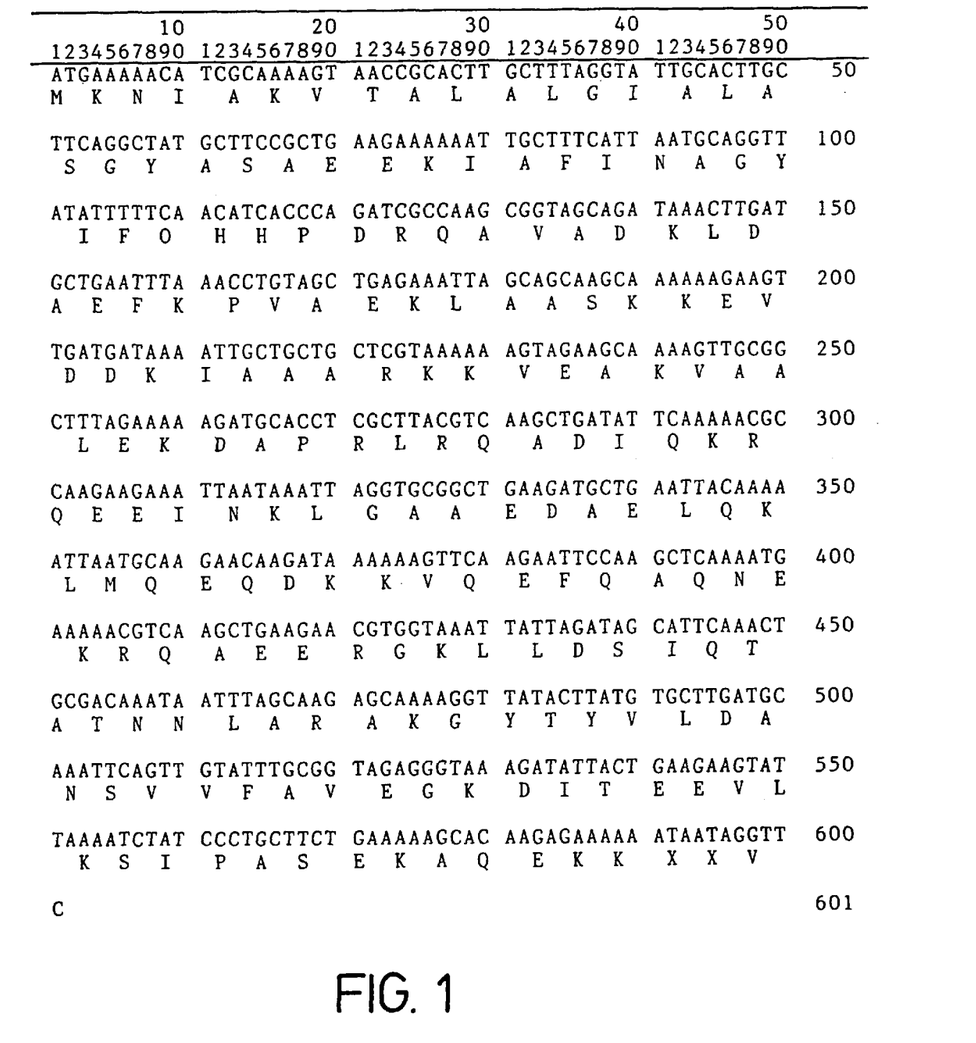
FIG. 1: shows the DNA sequence (SEQ ID NO:1) coding for OMP26 and the amino acid sequence (SEQ ID NO:2) derived from that DNA sequence.

In particular, the protein of the invention has the amino acid sequence shown in FIG. 1, or one substantially homologous thereto. In a separate embodiment, the protein of the invention has the amino acid sequence shown in FIG. 1 commencing from amino acid no. 24, or one substantially homologous thereto. The first 23 amino acids constitute a "signal" sequence and it will be appreciated that a protein minus this sequence will be equally applicable. The protein of the invention is an immunogen and is thus capable of inducing an immune response which will protect against infection with *H. influenzae*.

In the context of the present invention proteins which are "substantially homologous" to OMP26 may be 40%, 50%, 60%, 70%, 80%, 90%, 95% or even 99% homologous. Preferably, the protein will be at least 70% homologous, more preferably 80% homologous, even more preferably 90% homologous and most preferably 95% homologous. The skilled man will appreciate that the percentage degree of homology is one factor only. What is important is that the protein retains its antigenic effect. Thus, it is reasonable to have a protein having a relatively low degree of homology, for instance 40%, while retaining the antigenic activity discussed herein.

In addition, it is known in the art that "conservative" or indeed "semi-conservative" changes can be made to the amino acid sequence of a protein which will not alter its fundamental activity. For example, amino acids such as glycine, valine, leucine and isoleucine, which all have aliphatic side chains, may often be substituted for each other without substantially altering the biological activity of the protein. Similarly, amino acids such as phenylalanine, tyrosine and tryptophan, which all have aromatic side chains, may be substituted for each other. Such proteins which retain the antigenic effect described herein are within the scope of the present invention.

It is also possible that antigenic parts or regions of OMP26 can be employed to induce the protective effect against *H. influenzae*. Such antigenic parts or regions are also within the scope of the present invention.

In a second aspect, the present invention provides a nucleic acid sequence, preferably DNA, which codes for a protein of the invention, variants thereof as described above or indeed antigenic parts or regions. In particular, the invention provides a DNA sequence as shown in FIG. 1 which codes for OMP26. The skilled man will appreciate that due to the degeneracy of the genetic code it is possible to make conservative changes to the DNA sequence which will not result in changes to the amino acid sequence of the protein. Thus, such DNA sequences are also within the scope of the present invention. Suitably, nucleic acid of the invention can form part of a vector such as a plasmid.

As discussed herein, the proteins of the invention stimulate an immune response against *H. influenzae* and thus, in a third aspect, the present invention provides a vaccine formulation comprising a protein of the invention, as defined herein, optionally together with one or more carriers and/or adjuvants.

In a fourth aspect, the invention provides the use of the protein of the invention, as defined herein, in the preparation of a vaccine against *H. influenzae*.

The vaccine composition of the invention can be used to immunize a subject against *H. influenzae* infection. Therefore, the invention provides, in a fifth aspect, a method of immunizing a subject against infection by *H. Influenzae*, which comprises administering to the subject a vaccine composition of the invention. The vaccine compositions of the invention can be used to produce both systemic immunity and/or mucosal immunity.

In a sixth aspect, the present invention provides a method for the prophylaxis or treatment of respiratory tract infections or otitis media which comprises the step of administering to a subject a vaccine composition of the invention.

In other aspects the invention provides:
(a) The use of a protein of the invention, as defined herein, in the diagnosis of *H. Influenzae* infection; and
(b) A kit for use in the diagnosis of *H. Influenzae* infection comprising a protein of the invention, as defined herein.

Preferred features of each aspect of the invention are equally preferred for each other aspect mutatis mutandis.

The invention will now be described with reference to the following examples, which should not be construed as in any way limiting the invention.

The examples refer to the figures in which.

and

In the following example, the data have been expressed as the means +/− standard errors of the means. The pulmonary clearance data, total numbers of phagocytic cells, and differential cell count data were compared for statistical significance between groups by one-way analysis of variance, followed by Tuckey's test for multiple-comparison analysis (Macintosh Systat). Antibody data was assessed for between group significance by an unpaired t-test, and lymphocyte proliferation data assessed by a fully factorial analysis of variance (Macintosh Systat). Linear correlation between two variables was determined using the Pearson correlation coefficient (Macintosh Systat).

EXAMPLE 1

(i) Protein purification.

A 26 kDa protein (OMP26) was purified from strain NTHI-I by preparative electrophoresis. Bacteria from overnight culture of 100 agar plates were harvested by scraping the plates, and washed twice by centrifugation at 10,000× g for 10 min at 4° C. A crude outer membrane preparation was obtained by extraction of the outer membrane component with buffered Zwittergent 3-14 detergent and ethanol precipitation. The outer membrane extract was lyophilised, resuspended in a minimal amount of distilled water and further dissolved in 4 times the volume of sodium dodecyl sulfate (SDS) reducing buffer (62.5 mM Tris, [pH 6.8], 10% [vol/vol] glycerol, 2% [wt/vol] SDS, 5% [vol/vol] P-mercaptoethanol, $1.2 \times 10^{-3}$% [wt/vol] bromopheno blue). The SDS-preparation was incubated at 37° C. for at least 30 min prior to being located onto the stacking gel of the electrophoresis column. OMP26 was purified using preparative polyacrylamide electrophoresis (PAGE). Preparative SDS-PAGE to purify OMP26 was performed using the Bio-Rad Model 491 Prep Cell using a 60 ml 14 T-1.42% C. acrylamide/BIS (N,N'-methylene-bis acrylamide) separating gel with a 10 ml 4% T-0.36% C acrylamide/BIS stacking gel polymerised in a 37 mm (internal diameter [i.d.]) column. Fractions eluted from the column were concentrated by lyophilisation, and analysed for protein content by analytical SDS-PAGE. OMP26, isolated using these conditions, contained SDS which was subsequently removed by potassium phosphate and precipitation. Fractions containing OMP26 were pooled and dialysed prior to determination of protein concentration.

Analytical identification of the protein was performed by analytical SDS-PAGE using either gradient 10–15% or homogenous 12.5% acrylamide gels, and silver stained. Protein concentration was determined using the Pierce micro BCA assay. The presence of LOS was assessed by both silver staining of SDS-PAGE mini-gels and assaying with the E-TOXATE Limulus lysate test.

Results

Figure 2:
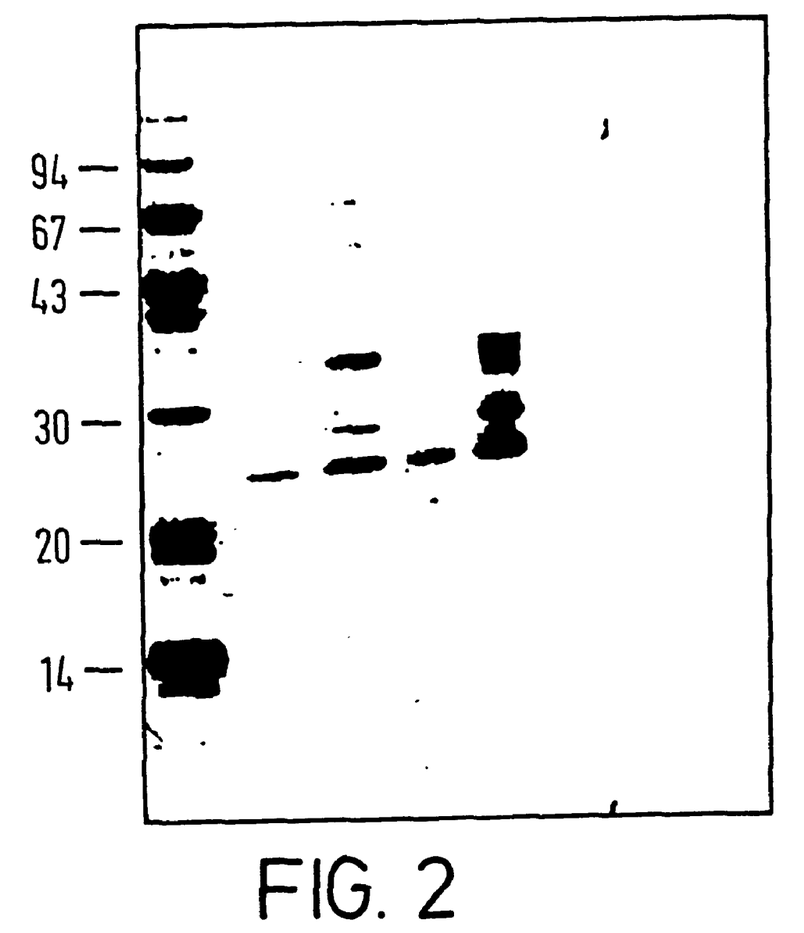
FIG. 2: shows SDS-PAGE analysis of OMP26 and two other proteins with higher molecular mass.

OMP26 was successfully separated from a group of three proteins with molecular masses between 26 and 30 kDa. FIG. 2 shows the position of this protein in relation to the other two, and the silver stained gel indicates the high degree of purity of the resulting preparation. Assessment of the heat-modifiable characteristic of this protein was performed by heating the protein sample at 100° C. for 30 min in the presence of β-mercaptoethanol. It was found that after 30 min the boiled protein sample still migrated with the same molecular mass (FIG. 2). To determine whether one of the other neighbouring protein bands may have been the heat-modifiable P5, all three proteins within this mass range were boiled for 30 min in the presence of β-mercaptomethanol, with none of the proteins demonstrating heat-modifiable characteristics (FIG. 2). Assessment of the protein for the presence of LOS contamination was performed using the E-TOXATE assay kit and found to be less than 0.6 μg endotoxin per mg protein.

(ii) Preparation of OMP26 for N-terminal Amino Acid Sequencing.

OMP26 was prepared for N-terminal amino acid sequence analysis by transferring the protein band from an SDS-PAGE gel to PVDF membrane. This protein sample was sent to Cortecs Diagnostic, Techbase 1, Newtech Square, Deeside, Clwyd, United Kingdom, for sequence analysis.

Amino Acid Sequence Identification

Figure 3:
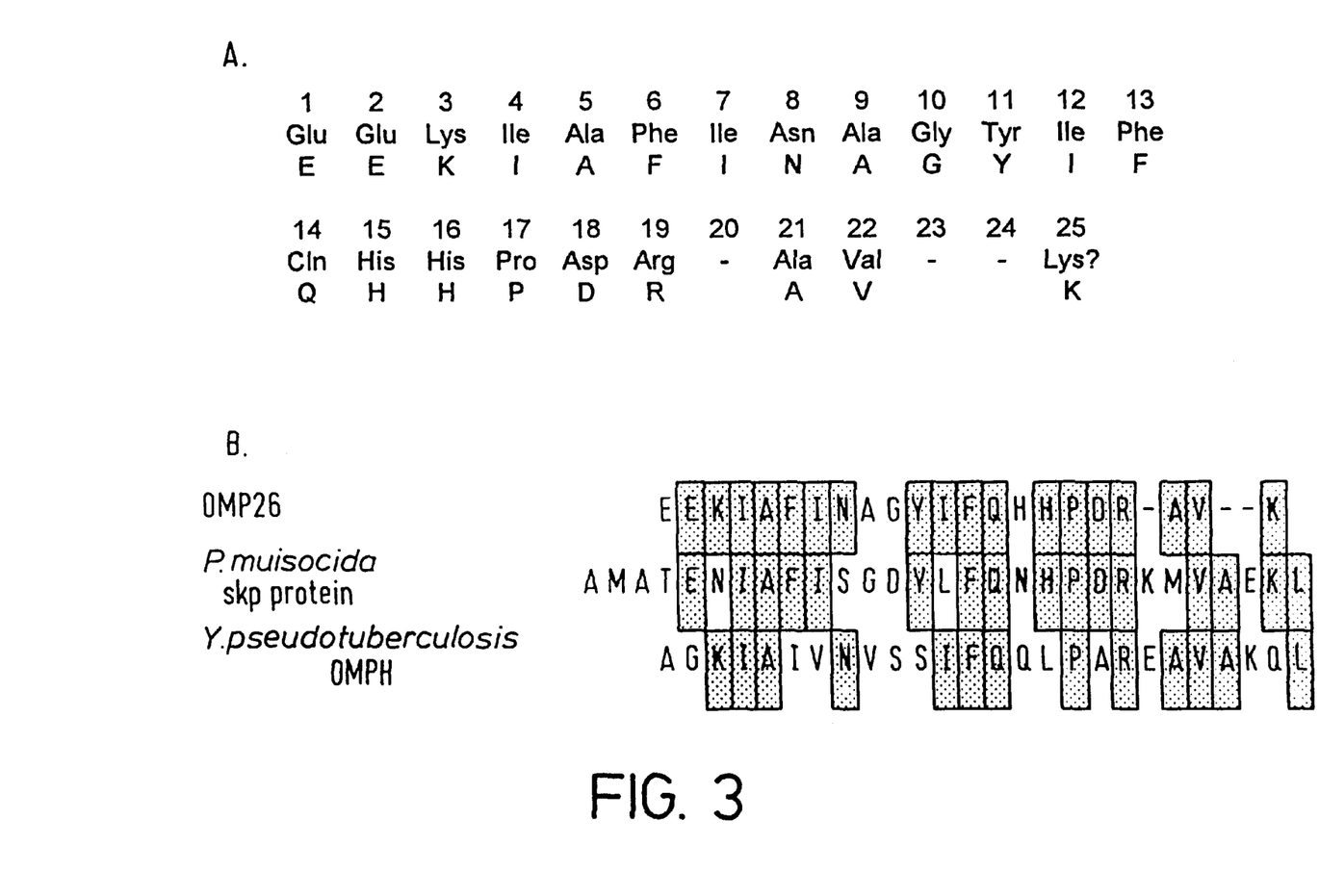
FIG. 3: shows the N-terminal sequence (SEQ ID NO;3) of the first 25 amino acids residues of OMP26 (a) and also a comparison of this with proteins from *P. multocida* (SEQ ID NO;4) and *Y. pseudotuberculosis* (SEQ ID NO;5)

An N-terminal amino acid sequence was obtained from the protein band transferred to PVDF. Amino acid sequence analysis for the first twenty-five peptides is shown in FIG. 3. The sequence analysis indicates no sequence homology with the N-terminal sequence of either Hib P5 or the fimbrin protein. The N-terminal amino acid sequence did show a 56% homology with a 21.4 kDa protein from *Pasteurella multocida* and a 44% sequence homology with a 19 kDa outer membrane protein from *Yersinia pseudotuberculosis*.

(iii) Immunisation and Bacterial Challenge

Specific pathogen-free male rats received an intra-Peyer's patch (IPP) immunisation on day 1, an intra-tracheal (IT) boost on day 14, and the final live bacterial challenge on day 21. The animals were sedated with halothane to facilitate intravenous anaesthesia with chloral hydrate via the tail vein. The small intestine was exposed through a mid-line abdominal incision and the antigen injected subserosal to each Peyer's patch using a 27-guage needle. The immunization protein (OMP26) was prepared by emulsification of 200 or 800 μg of protein per ml in a 1:1 ratio of Incomplete Freund's adjuvant (IFA) and phosphate buffered saline (PBS), and a total inoculum of 10 or 40 μg protein respectively was administered to each animal. Two control groups of rats consisted of (i) a mixture of untreated and sham-immunised groups (immunized with IFA and PBS), and (ii) a positive group immunized with killed bacteria of the homologous NTHI strain. Rats received an IT boost on day 14, post-IPP immunization. OMP26-immunized rats received an IT boost of 10 μg of OMP26. The non-immune group received 50 μl PBS, while the killed bacteria-immunised group received 50 μl of killed bacteria (bacteria count of $10^{10}$ per ml). Animals were challenged for 4 hours with live bacteria (bacteria count $5 \times 10^8$) 21 days after the first immunization. A heterologous strain, NTHI-II, was also used for bacterial challenge. Bacteria were grown overnight at 37° C. in 5% $CO_2$ on brain heart infusion agar plates supplemented with 50 ml defibrinated horse blood per litre of agar, recovered, washed and resuspended in PBS to the required concentration. Bacteria were introduced into the lungs via an intra-tracheal cannula and 4 hours later the rats were euthanised. Blood was collected and aliquots of serum stored at −20° C. for antibody analysis. Lungs were lavaged by flushing with 5×2 ml of PBS, and the pooled lavage (BAL) assessed for bacteria numbers. Following lung lavage, the lungs were removed, homogenised and assessed for numbers of bacteria. Cytospin slides were prepared for determination of differential cell counts in the lung lavage. Total cell numbers present in the lung lavage were calculated by staining with methylene blue and counting using a haemocytometer.

Results

Figure 4:
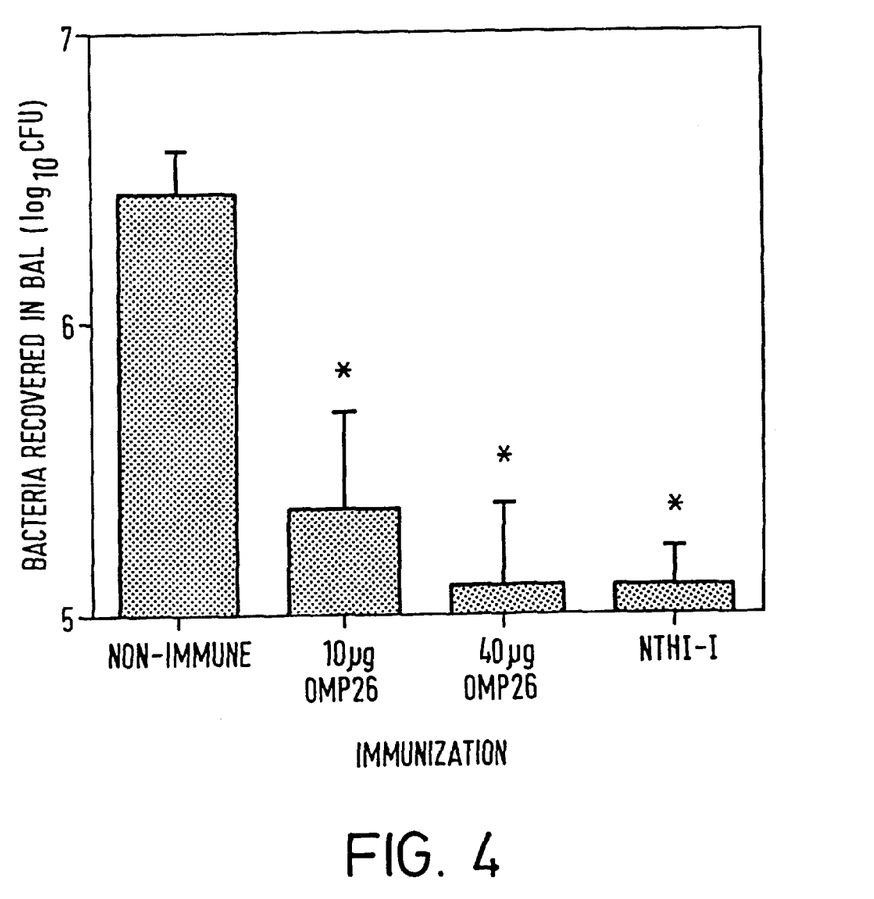
FIG. 4: shows NTHI-I bacteria recovered in bronchial washings 4 hr post-challenge with live bacteria.

Rats immunized with OMP26 and challenged with live bacteria of the NTHI-I homologous strain on day 21 showed significant bacterial clearance (P<0.005). Rats immunized and boosted with 10 μg OMP26 had 92% fewer bacteria in the lung than the non-immune group after 4 h, whereas rats receiving 40 μg OMP26 in the IPP immunization, and boosted with 10 µg OMP26, had 96% fewer bacteria and were equivalent to the 95% clearance observed for killed bacteria immunized rats (FIG. 4).

Rats immunized with OMP26 were also challenged with live bacteria from a heterologous nontypeable strain, NTHI-II. The results in Table 1 show that OMP26 immunization also significantly (P<0.005) cleared bacteria in a pulmonary challenge by a different strain. The immunized group had 93% fewer bacteria than the non-immune group in the BAL after 4 h, demonstrating a rate of bacterial clearance comparable to that for homologous challenge. OMP26 immunization also reduced the numbers of bacteria present in the lung homogenates of the immunized groups compared with the non-immune groups. The lung homogenates from the rats challenged with NTHI-II (heterologous strain) had significantly less bacteria than the non-immune lungs. However, the magnitude of the difference was 80% in the lungs, with 93% clearance in the BAL as compared with 89% clearance in the lungs, and 87% clearance in the BAL for groups challenged with NTHI-I (the homologous strain). The percentage clearance in this experiment for NTHI-I differed from previous experiments due to the live bacterial inoculum containing considerably more bacteria than usual (usual inoculum ranged between 0.6 and $1.4 \times 10^{10}$ CFU per ml).

Greater numbers of phagocytic cells were present in the BAL of OMP26-immunized animals, and correlated with the enhanced bacterial clearance in these animals (Table 2). The increase in cell recruitment in immunized groups was the same for both homologous and non-homologous bacterial challenge. However, at 4 h post-challenge, the differential cell counts were not significantly different between immune and non-immune groups (Table 2), with both groups showing similar ratios of PMNs to macrophage:

TABLE 1

Pulmonary clearance following OMP-26 immunization with challenge by homologous and heterologous non-typeable *H. influenzae* bacteria.

| | | *H. influenzae* recovered 4 h post-challenge ($\log_{10}$CFU)[a] (% clearance) Challenge strain of *H. influenzae*[b] | |
|---|---|---|---|
| Rat group[c] | | NTHI-I (homologous) | NTHI-II (heterologous) |
| Non-immune | BAL | 7.01 ± 0.11 | 6.28 ± 0.07 |
| | Lung | 7.76 ± 0.05 | 6.69 ± 0.05 |
| OMP26-immunized | BAL | 6.15 ± 0.15 (87%)* | 5.15 ± 0.16 (93%)* |
| | Lung | 6.81 ± 0.17 (89%)* | 6.01 ± 0.19 (80%)* |

[a]Values represent mean ± SEM in either the BAL or lung homogeneic for rats challenged for 4 h with live bacteria from either NTHI-I or NTHI-II strains on day 21 post-PP immunization with 10 µg OMP26. All rats received an IT-boost (10 µg) on day 14. Non-immune rats were a combination of sham-treated and untreated animals.
[b]Concentration of live bacterial in challenge inoculum (as determined by plating of serial dilutions) was 10.38 ($\log_{10}$) CFU per ml for NTHI-I and 10.17 ($\log_{10}$) CFU per ml for NTHI-II.
[c]n = 4 per group for challenge with NTHI-I
n = 4 for non-immune and n = 6 for OMP26-immunized groups for challenge with NTHI-II
*P < 0.001 compared to non-immune group.

TABLE 2

Phagocytic cell counts in the BAL 4 h post-pulmonary challenge with five non-typeable *H. influenzae*.

| | Challenged with NTHI-I (homologous) | Challenged with NTHI-II (heterologous) | Differential cell count from cytospin slide preparation of BAL (%) | | |
|---|---|---|---|---|---|
| Rat group | Total number of cells in BAL (× $10^6$) | | PMNs | Macrophages | Others |
| Non-immune | 15.9 ± 1.1 | 17.5 ± 3.0 | 95.8 | 2.2 | 2 |
| OMP26-immunized | 26.1 ± 1.1[n] | 28.2 ± 1.6[n] | 95 | 2.7 | 2.1 |

[n]P < 0.001 compared to non-immune group.

(iv) OMPS26-specific ELISA.

Polysorb microtiter wells were coated with purified OMP26 at a concentration of 1 µg per ml for assay of IgG, $IgG_{2a}$, IgA, and IgM; and 10 µg per ml for $IgG_1$, $IgG_{2b}$, $OgG_{2c}$ and IgE. The plates were washed five times in PBS containing 0.05% Tween 20 between incubation steps. The wells were blocked with 5% skim milk in PBS-0.05% Tween 20 for 60 min. Wells were incubated for 90 min with serum (1/25 to 1/3200), or BAL (1/2 to 1/16) samples were serially diluted in blocking buffer for analysis. Conjugated immunoglobulin used were goat anti-rat IgG (1/2000), IgA (1/1000), and IgM (1/4000) (Fc specific); mouse anti-rat $IgG_1$ (1/500), $IgG_{2a}$ (1/1000), $IgG_{2b}$ (1/500), and $IgG_{2c}$ (1/500), and wells were incubated with conjugated immunoglobulin for 90 min. The plates were then developed.

Results

Antibody specific to OPM26 was measured in the serum and BAL samples of rats immunized with OMP26, as well as from rats that had been immunized with killed bacteria from four different strains of *H. Influenzae*. High OMP26-specific antibody titers for IgG, IgA and IgM were found in the serum, and IgG and IgA in the BAL of rats immunized with OMP26, with the highest levels observed for the group receiving the higher immunization dosage of 40 µg (Table 3). Detectable levels of OMP26-specific IgG, IgA and IgM in the serum, and IgG and IgA in the BAL, were also found in rats that had been immunized with different strains of *H. Influenzae* (Table 3), although the levels observed for these groups were significantly less than those in the OMP26-immunized groups. IgE ELISAs were also carried out on serum from OMP26 rat groups, however, levels of OMP26-specific IgE could not be detected (data not shown).

Figure 5:
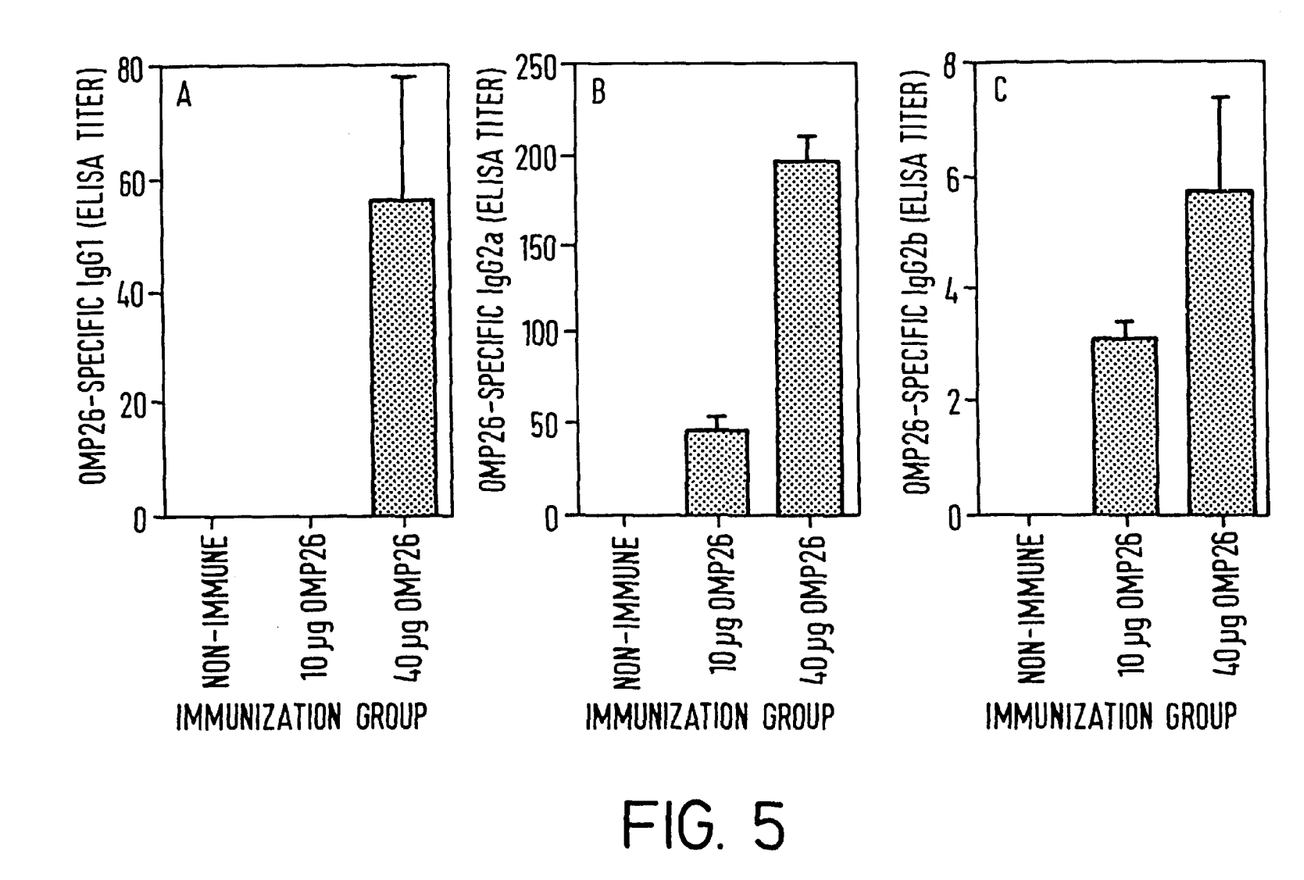
FIG. 5: shows OMP26-specific levels of IgG subclasses in serum of rats immunized with OMP26.

Measurement of OMP26-specific IgG subclasses found that OMP26-specific $IgG_1$ was only detectable following the 40 µg immunization, whereas significant levels of $IgG_{2a}$ and $IgG_{2b}$ subclasses were found for both 10 µg and 40 µg OMP26 immunization groups (FIG. 5). Levels of both $IgG_{2a}$ and $IgG_{2b}$ increased significantly (P<0.05) with the increase in concentration of OMP26 from 10 µg to 40 µg in the IPP inoculum. $IgG_{2c}$ was also measured, however, significant levels of OMP26-specific antibody from this subclass could not be detected (data not shown).

TABLE 3

Comparison of OMP26-specific antibodies in serum and bronchoalveolar lavage following immunization with either OMP26 or killed bacteria from *H. influenzae*.

| | | Antibody to OMP26 (ELISA titer[a]) | | | | | |
|---|---|---|---|---|---|---|---|
| | | Serum | | | Bronchoalveolar Lavage | | |
| Group[b] | n | IgG | IgA | IgM | IgG | IgA | IgM |
| Non-immune | 7 | n.d.[d] | n.d. | 10.5 ± 1.6 | n.d. | n.d. | n.d. |
| 10 μg OMP26 | 5 | 1209 ± 255* | 936 ± 161* | 30.5 ± 4* | 4.3 ± 1.0* | 6.1 ± 1.9* | n.d. |
| 40 μg OMP26 | 5 | 2806 ± 405* | 2440 ± 410* | 142.5 ± 30.6* | 8.3 ± 1.9* | 29.1 ± 7.9* | n.d. |
| NTHI-I[c] | 4 | 58 ± 17* | 37 ± 4* | 39.1 ± 0.8* | 0.5 ± 0.1 | 1.2 ± 0.5 | n.d. |
| NTHI-II[c] | 4 | 22 ± 4* | 26 ± 5* | 39.3 ± 5.0* | 0.6 ± 0.1 | 0.4 ± 0.1 | n.d. |
| HI-CD[c] | 4 | 18 ± 1* | 20 ± 1* | 42.2 ± 3.1* | 0.6 ± 0.1 | 0.8 ± 0.3 | n.d. |
| Hib-II[c] | 4 | 27 ± 4* | 38 ± 3* | 34.4 ± 2.3* | 0.6 ± 0.1 | 1.6 ± 0.4 | n.d. |

[a]Antibody titers calculated as described in the materials and methods.
[b]Rats were immunized via PP on day 0, received an IT boost on day 14 and were challenged with live bacteria on day 21. Serum and BAL samples were prepared as described in the materials and methods.
[c]Rats were immunized with killed bacteria from the strain of *H. influenzae* indicated and had received a live challenge with bacteria from the homologous strain.
[d]n.d. indicates that OMP26-specific antibody could not be detected at the lowest sample dilution.
*P < 0.05 compared to non-immune group.

(v) Immunoblot.

Proteins separated by SDS-PAGE were electrophoretically transferred to nitrocellulose (0.2 μm pore size). Rat serum from OMP26, NTHI-I, NTHI-II, as well as strains HI-CD, and Hib-II-immunized groups was diluted 10-fold in TTBS-5% (w/v) skim milk powder and was used as the primary antibody. A 500-fold dilution of horseradish peroxidase conjugated goat anti-rat IgG (Fc specific) in TTBS-5% skim milk was used as the second antibody.

Results

Figure 6:
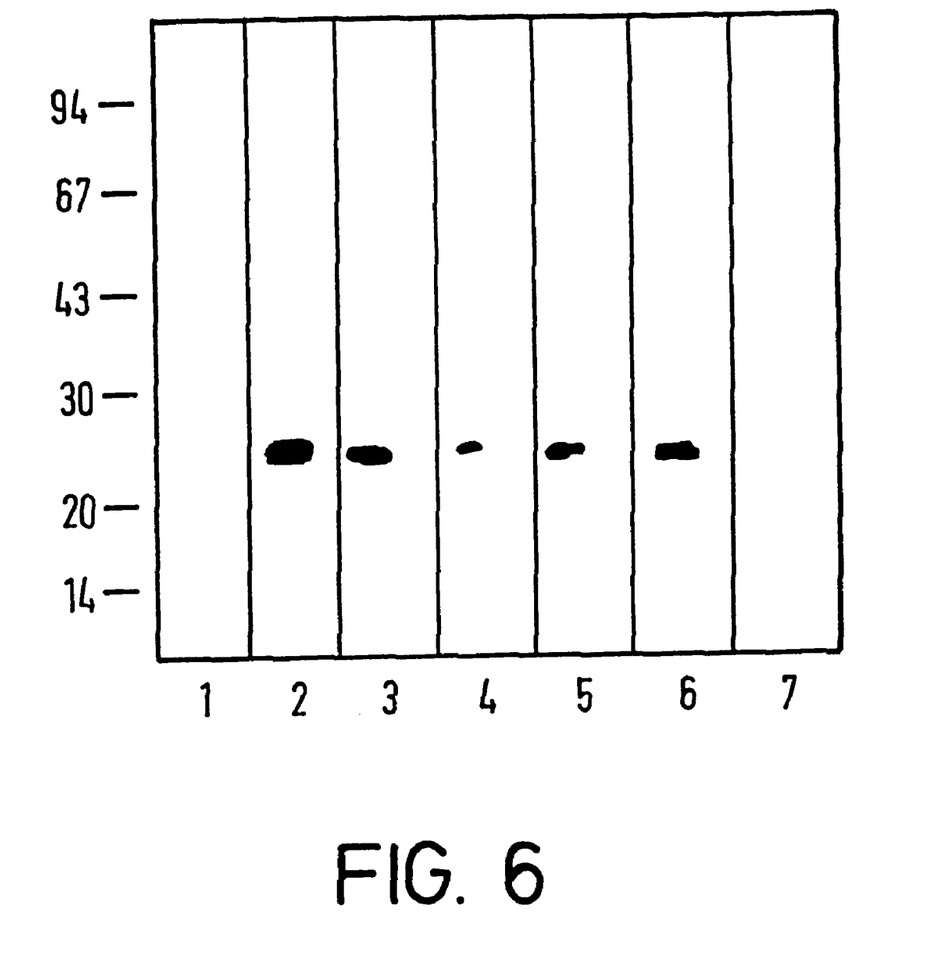
FIG. 6: shows an Immunoblot for the detection of OMP26-specific antibody in serum.

Immunoblot analysis of recognition of OMP26 by antibodies present in the serum of non-immune, OMP26-immunized and *H. Influenzae*- (four strains) immunized rats has shown recognition of this protein by antibodies present in the serum from each of the immunized groups, but not the non-immune group (FIG. 6). This demonstrates the cross-reactivity of antibody-responses generated by immunization with the *H. Influenzae* strains used in this study with the OMP26 purified from the NTHI-I strain.

(vi) Antigen-Specific Lymphocyte Assay.

Lymphocytes obtained from the mesenteric lymph nodes (MLN) were cultured at a concentration of $10^6$ cells per ml. The antigen (OMP26) was suspended in culture medium in a 10-fold dilution series and sterile filtered. The cell suspension and antigen were added in triplicate to flat-bottomed multiwell plates to give a final volume of 0.2 ml per well. Lymphocyte proliferation was estimated by [$^3$H] thymidine incorporation for the last 8 h of a 4-day culture. Results were calculated by subtraction of background from the geometric means of triplicate wells, then the geometric mean +/− standard error of the entire treatment group.

Results

Figure 7:
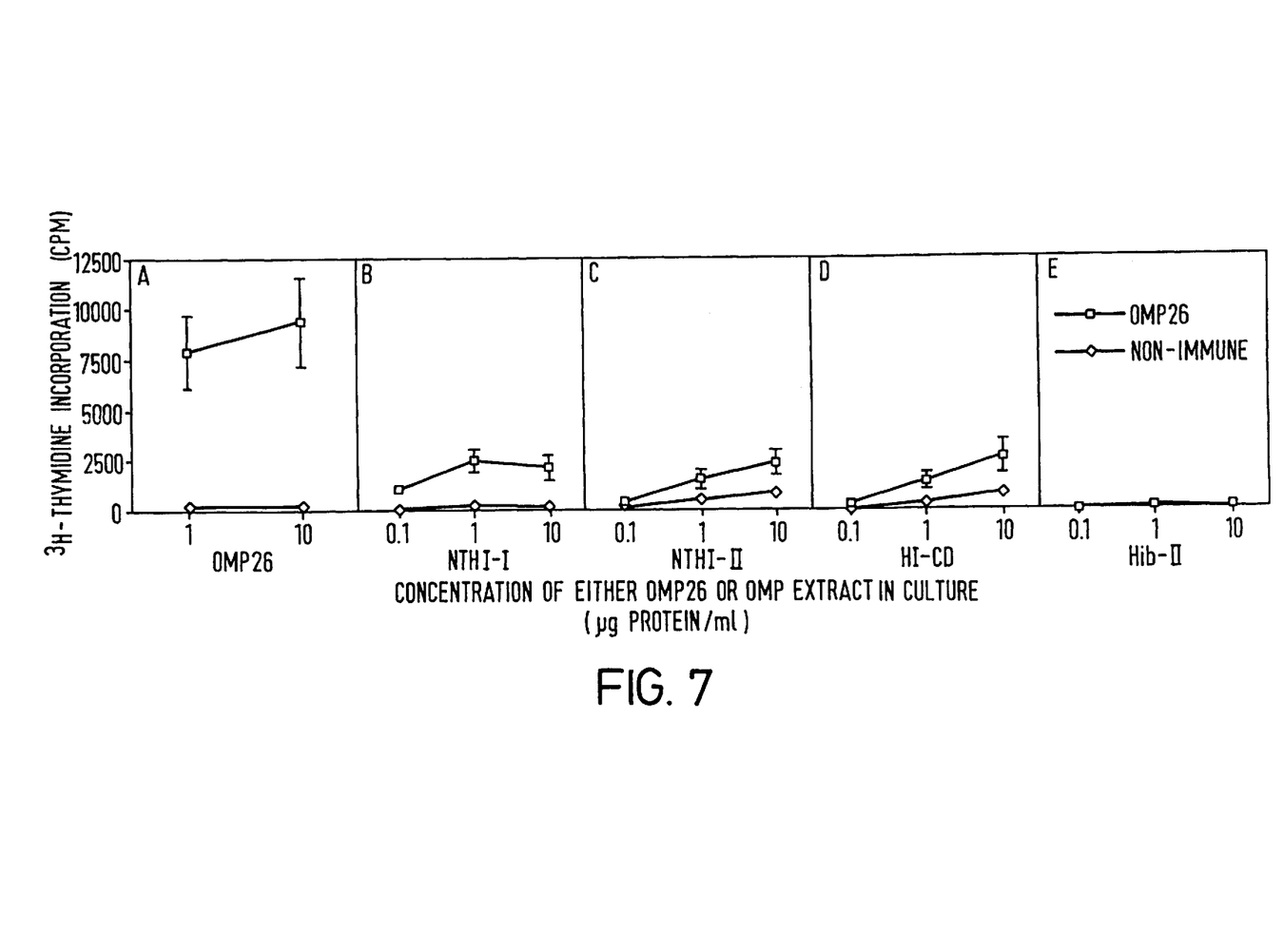
FIG. 7: shows Antigen-specific proliferation of lymphocytes isolated from the MLN of OMP26 immunized and non-immune rats.

Lymphocytes from the MLN of OMP26-immunized and non-immunized rats were assessed for antigen-specific proliferative responses. Cells from the OMP26-immunized group responded significantly to OMP26 in culture in vitro, whereas cells from the non-immunized rats did not show significant proliferation (FIG. 7A). The lymphocytes from rats immunized with OMP26 were also cultured with OMP extracts from four *H. Influenzae* strains to assess cross-reactive responses. Significant proliferative responses were found in the lymphocytes from the OMP26-immunized group for the OMP extracts from strains NTHI-I, NTHI-II and HI-CD, but no significant proliferation was observed for the extract from the Hib-II strain (FIGS. 7B–E).

EXAMPLE 2: CLONING AND SEQUENCING OF OMP26

DNA was extracted from NTHi. The region of DNA encoding OMP26 was identified and amplified by standard PCR methods using primers designed to recognise the gene (synthesised at Biomolecular Resource Facility, John Curtin School of Medical Research, Canberra, ACT, Australia). After analysis to determine successful recognition of the correct product, the PCR DNA product was extracted.

Two plasmids were prepared. One DNA product contained the region encoding both the signal peptide and the mature OMP26 product and the second encoded the final mature OMP26 (without the leader signal peptide). The PCR DNA products were digested with the endonucleases Hindiii for OMP26 plus signal peptide and NspBII plus HindIII for mature OMP26. The digested DNA was recovered and ligated at the SmaI and HindIII sites into the plasmids pQE30 or pQE31 (Giagen GmbH, Hilden, Germany) for OMP26 plus signal peptide or OMP26 mature protein respectively. The plasmids were then purified and precipitated. sequencing was performed by the dye deoxy-terminator procedure at the biomolecular resource Facility, John Curtin School of Medical Research, Canberra, Australia.

Results

The sequence shown in FIG. 1 represents both the mature OMP26 plus the signal peptide. The signal peptide sequence encompasses the first twenty-three amino acids. The final product expressed by NTHi on the outer membrane commences at amino acid twenty-four.

What is claimed:

1. A vaccine formulation comprising an isolated protein which (i) is an outer membrane protein of *Haemophilus influenzae* or an immunogenic fragment thereof and (ii) comprises the amino acid sequence as set forth in SEQ ID NO.2, an immunogenic fragment of said sequence, a sequence at least 90% identical to the amino acid sequence as set forth in SEQ ID NO.2 and having an immunogenic epitope of SEQ ID NO:2 or an immunogenic fragment of a sequence at least 90% identical to the amino acid sequence as set forth in SEQ ID NO.2 wherein said fragment has an immunogenic epitope of SEQ ID NO:2, together with one or more carriers and/or adjuvants.

2. A vaccine formulation as claimed in claim 1, wherein the isolated protein or immunogenic fragment thereof comprises an amino acid sequence at least 95% identical to the amino acid sequence as set forth in SEQ ID NO.2 and having an immunogenic epitope of SEQ ID NO:2 or an immunogenic fragment of a sequence at least 95% identical to the amino acid sequence as set forth in SEQ ID NO.2 wherein said fragment has an immunogenic epitope of SEQ ID NO:2.

3. A vaccine formulation comprising an isolated protein or immunogenic fragment thereof, which comprises an amino acid sequence as set forth in SEQ ID NO.2 commencing with amino acid twenty-four as the N-terminal amino acid, an immunogenic fragment of said sequence, a sequence at least 90% identical to the amino acid sequence as set forth in SEQ ID NO.2 commencing with amino acid twenty-four as the N-terminal amino acid and having an immunogenic epitope of SEQ ID NO:2 commencing with amino acid twenty-four as the N-terminal amino acid, or an immunogenic fragment of a sequence at least 90% identical to the sequence as set forth in SEQ ID NO.2 commencing with amino acid twenty-four as the N-terminal amino acid wherein said fragment has an immunogenic epitope of SEQ ID NO:2 commencing with amino acid twenty-four as the N-terminal amino acid, together with one or more carriers and/or adjuvants.

4. A vaccine formulation as claimed in claim 3 wherein the isolated protein or immunogenic fragment thereof comprises an amino acid sequence which is at least 95% identical to the amino acid sequence as set forth in SEQ ID NO.2 commencing with amino acid twenty-four as the N-terminal amino acid and having an immunogenic epitope of SEQ ID NO:2 commencing with amino acid twenty-four as the N-terminal amino acid, or an immunogenic fragment of a sequence at least 95% identical to the amino acid sequence as set forth in SEQ ID NO.2 commencing with amino acid twenty-four as the N-terminal amino acid wherein said fragment has an immunogenic epitope of SEQ ID NO:2 commencing with amino acid twenty-four as the N-terminal amino acid.

5. A vaccine formulation as claimed in claim 1, wherein the isolated protein or immunogenic fragment thereof, forms part of a fusion protein.

6. A vaccine formulation as claimed in claim 3, wherein the isolated protein or immunogenic fragment thereof, forms part of a fusion protein.

7. A kit for use in the diagnosis of *H. Influenzae* infection comprising an isolated protein or immunogenic fragment thereof, which comprises an amino acid sequence as set forth in SEQ ID No.2 commencing with amino acid twenty-four as the N-terminal amino acid, an immunogenic fragment of SEQ ID NO:2, a sequence at least 90% identical to the amino acid sequence as set forth in SEQ ID NO.2 commencing at amino acid twenty-four as the N-terminal amino acid and having an immunogenic epitope of said SEQ ID NO. 2, or an immunogenic fragment of a sequence at least 90% identical to the sequence as set forth in SEQ ID NO.2 commencing at amino acid twenty-four as the N-terminal amino acid and having an immunogenic epitope of SEQ ID NO:2.

8. A kit as claimed in claim 7, wherein the isolated protein or immunogenic fragment thereof comprises an amino acid sequence at least 95% identical to the amino acid sequence as set forth in SEQ ID NO.2 commencing with amino acid twenty-four as the N-terminal amino acid and having an immunogenic epitope of SEQ ID NO:2, or an immunogenic fragment of a sequence at least 95% identical to the sequence as set forth in SEQ ID NO.2 commencing at amino acid twenty-four as the N-terminal amino acid wherein said fragment has an immunogenic epitope of SEQ ID NO:2.

9. A kit for use in the diagnosis of *H. Influenzae* infection comprising an isolated protein or immunogenic fragment thereof which comprises an amino acid sequence as set forth in SEQ ID NO.2, an immunogenic fragment of said sequence, a sequence at least 90% identical to the amino acid sequence as set forth in SEQ ID NO.2 and having an immunogenic epitope of SEQ ID NO:2 or an immunogenic fragment of a sequence at least 90% identical to the sequence as set forth in SEQ ID NO.2 wherein said fragment has an immunogenic epitope of SEQ ID NO:2.

10. A kit as claimed in claim 9, wherein the isolated protein or immunogenic fragment thereof comprises an amino acid sequence at least 95% identical to the amino acid sequence as set forth in SEQ ID NO.2 and having an immunogenic epitope of SEQ ID NO:2 or an immunogenic fragment of a sequence at least 95% identical to the amino acid sequence as set forth in SEQ ID NO.2 wherein said fragment has an immunogenic epitope of SEQ ID NO:2.

11. An isolated protein, wherein the protein comprises an amino acid sequence as set forth in SEQ ID No.2 or a sequence at least 90% identical thereto which comprises an immunogenic epitope of SEQ ID NO:2.

12. An isolated protein as claimed in claim 11 wherein the protein comprises an amino acid sequence which is at least 95% identical to the amino acid sequence as set forth in SEQ ID No.2 and comprises an immunogenic epitope of SEQ ID NO:2.

13. An isolated protein wherein the protein comprises an amino acid sequence as set forth in SEQ ID NO.2 commencing at amino acid twenty-four as the N-terminal amino acid or a sequence at least 90% identical to said sequence and comprises an immunogen epitope of SEQ ID NO:2.

14. An isolated protein as claimed in claim 13, wherein the protein comprises an amino acid sequence which is at least 95% identical to the amino acid sequence as set forth in SEQ ID NO.2 commencing at amino acid twenty-four as the N-terminal amino acid and comprises an immunogenic epitope of SEQ ID NO:2.

15. A fragment of the isolated protein of claim 11, wherein said fragment comprises an immunogenic epitope of an amino acid sequence as set forth in SEQ ID NO.2 or a sequence at least 90% identical thereto and having an immunogenic epitope of SEQ ID NO:2.

16. A fragment as claimed in claim 15, wherein said fragment comprises an immunogenic epitope of an amino acid sequence which is at least 95% identical to the amino acid sequence as set forth in SEQ ID NO.2 and wherein said fragment has an immunogenic epitope of SEQ ID NO:2.

17. A fragment of the isolated protein of claim 13, wherein said fragment comprises an immunogenic epitope of an amino acid sequence as set forth in SEQ ID NO.2 commencing with amino acid number twenty-four as the N-terminal amino acid or a sequence at least 90% identical to said sequence and having an immunogenic epitope of SEQ ID NO:2.

18. A fragment as claimed 17, wherein said fragment comprises an immunogenic epitope of an amino acid sequence which is as set forth in SEQ ID NO.2 commencing with amino acid number twenty-four as the N-terminal amino acid or a sequence at least 95% identical to said sequence and having an immunogenic epitope of SEQ ID NO:2.

19. A vaccine formulation comprising an isolated protein which is an outer membrane protein of *Haemophilus influenzae* and comprises the amino acid sequence as set forth in SEQ ID NO.2 or an immunogenic fragment of said sequence.

20. A vaccine formulation as claimed in claim 19, wherein the isolated protein comprises the amino acid sequence as set forth in SEQ ID NO.2.

21. A vaccine formulation as claimed in claim 19, wherein the isolated protein comprises the amino acid sequence as set forth in SEQ ID NO.2 commencing with amino acid twenty-four as the N-terminal amino acid.

22. A vaccine formulation as claimed in claim 19, wherein the isolated protein comprises an immunogenic fragment of the amino acid sequence as set forth in SEQ ID NO.2.

23. A vaccine formulation as claimed in claim 19, wherein the isolated protein forms part of a fusion protein.

24. A kit for use in the diagnosis of *H. infliuenzae* infection comprising an isolated protein which comprises an amino acid sequence as set forth in SEQ ID NO.2 or an immunogenic fragment of said sequence.

25. A kit as claimed in claim 24, wherein the isolated protein comprises the amino acid sequence as set forth in SEQ ID NO.2.

26. A kit as claimed in claim 24, wherein the isolated protein comprises the amino acid sequence as set forth in SEQ ID NO.2 commencing with amino acid twenty-four as the N-terminal amino acid.

27. A kit as claimed in claim 24, wherein the isolated protein comprises an immunogenic fragment of the amino acid sequence as set forth in SEQ ID NO.2.

28. An isolated *Haemophilus influenzae* protein, which comprises the amino acid sequence as set forth in SEQ ID NO.2 or an immunogenic fragment of said sequence.

29. An isolated protein as claimed in claim 28, wherein the protein comprises the amino acid sequence as set forth in SEQ ID NO.2.

30. An isolated protein as claimed in claim 28, wherein the protein comprises the amino acid sequence as set forth in SEQ ID NO.2 commencing with amino acid twenty-four as the N-terminal amino acid.

31. An isolated protein as claimed in claim 28, wherein the protein comprises an immunogenic fragment of the amino acid sequence as set forth in SEQ ID NO.2.

* * * * *

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 601 base pairs
      (B) TYPE: nucleic acid
      (C) STRANDEDNESS: single
      (D) TOPOLOGY: linear    (ii) MOLECULE TYPE: cDNA    (vi) ORIGINAL SOURCE:
      (A) ORGANISM: Haemophilus influenzae    (ix) FEATURE:
      (A) NAME/KEY: CDS
      (B) LOCATION:1..594

(xi) SEQUENCE DESCRIPTION: SEQ ID NO: 1:

```
ATG AAA AAC ATC GCA AAA GTA ACC GCA CTT GCT TTA GGT ATT GCA CTT      48
Met Lys Asn Ile Ala Lys Val Thr Ala Leu Ala Leu Gly Ile Ala Leu
 1               5                  10                  15

GCT TCA GGC TAT GCT TCC GCT GAA GAA AAA ATT GCT TTC ATT AAT GCA      96
Ala Ser Gly Tyr Ala Ser Ala Glu Glu Lys Ile Ala Phe Ile Asn Ala
             20                  25                  30

GGT TAT ATT TTT CAA CAT CAC CCA GAT CGC CAA GCG GTA GCA GAT AAA     144
Gly Tyr Ile Phe Gln His His Pro Asp Arg Gln Ala Val Ala Asp Lys
         35                  40                  45

CTT GAT GCT GAA TTT AAA CCT GTA GCT GAG AAA TTA GCA GCA AGC AAA     192
Leu Asp Ala Glu Phe Lys Pro Val Ala Glu Lys Leu Ala Ala Ser Lys
 50                  55                  60

AAA GAA GTT GAT GAT AAA ATT GCT GCT GCT CGT AAA AAA GTA GAA GCA     240
Lys Glu Val Asp Asp Lys Ile Ala Ala Ala Arg Lys Lys Val Glu Ala
 65                  70                  75                  80

AAA GTT GCG GCT TTA GAA AAA GAT GCA CCT CGC TTA CGT CAA GCT GAT     288
Lys Val Ala Ala Leu Glu Lys Asp Ala Pro Arg Leu Arg Gln Ala Asp
                 85                  90                  95

ATT CAA AAA CGC CAA GAA GAA ATT AAT AAA TTA GGT GCG GCT GAA GAT     336
Ile Gln Lys Arg Gln Glu Glu Ile Asn Lys Leu Gly Ala Ala Glu Asp
             100                 105                 110

GCT GAA TTA CAA AAA TTA ATG CAA GAA CAA GAT AAA AAA GTT CAA GAA     384
Ala Glu Leu Gln Lys Leu Met Gln Glu Gln Asp Lys Lys Val Gln Glu
         115                 120                 125

TTC CAA GCT CAA AAT GAA AAA CGT CAA GCT GAA GAA CGT GGT AAA TTA     432
Phe Gln Ala Gln Asn Glu Lys Arg Gln Ala Glu Glu Arg Gly Lys Leu
 130                 135                 140

TTA GAT AGC ATT CAA ACT GCG ACA AAT AAT TTA GCA AGA GCA AAA GGT     480
Leu Asp Ser Ile Gln Thr Ala Thr Asn Asn Leu Ala Arg Ala Lys Gly
145                 150                 155                 160

TAT ACT TAT GTG CTT GAT GCA AAT TCA GTT GTA TTT GCG GTA GAG GGT     528
Tyr Thr Tyr Val Leu Asp Ala Asn Ser Val Val Phe Ala Val Glu Gly
                 165                 170                 175

AAA GAT ATT ACT GAA GAA GTA TTA AAA TCT ATC CCT GCT TCT GAA AAA     576
Lys Asp Ile Thr Glu Glu Val Leu Lys Ser Ile Pro Ala Ser Glu Lys
             180                 185                 190

GCA CAA GAG AAA AAA TAA TAGGTTC                                     601
Ala Gln Glu Lys Lys
         195
```

(2) INFORMATION FOR SEQ ID NO: 2:

(i) SEQUENCE CHARACTERISTICS:
        (A) LENGTH: 197 amino acids
        (B) TYPE: amino acid
        (D) TOPOLOGY: linear     (ii) MOLECULE TYPE: protein     (xi) SEQUENCE DESCRIPTION: SEQ ID NO: 2:

```
Met Lys Asn Ile Ala Lys Val Thr Ala Leu Ala Leu Gly Ile Ala Leu
 1               5                  10                  15

Ala Ser Gly Tyr Ala Ser Ala Glu Glu Lys Ile Ala Phe Ile Asn Ala
                20                  25                  30

Gly Tyr Ile Phe Gln His His Pro Asp Arg Gln Ala Val Ala Asp Lys
            35                  40                  45

Leu Asp Ala Glu Phe Lys Pro Val Ala Glu Lys Leu Ala Ala Ser Lys
    50                  55                  60

Lys Glu Val Asp Asp Lys Ile Ala Ala Arg Lys Lys Val Glu Ala
 65                  70                  75                  80

Lys Val Ala Ala Leu Glu Lys Asp Ala Pro Arg Leu Arg Gln Ala Asp
                85                  90                  95

Ile Gln Lys Arg Gln Glu Glu Ile Asn Lys Leu Gly Ala Ala Glu Asp
               100                 105                 110

Ala Glu Leu Gln Lys Leu Met Gln Glu Gln Asp Lys Lys Val Gln Glu
           115                 120                 125

Phe Gln Ala Gln Asn Glu Lys Arg Gln Ala Glu Glu Arg Gly Lys Leu
   130                 135                 140

Leu Asp Ser Ile Gln Thr Ala Thr Asn Asn Leu Ala Arg Ala Lys Gly
145                 150                 155                 160

Tyr Thr Tyr Val Leu Asp Ala Asn Ser Val Val Phe Ala Val Glu Gly
                165                 170                 175

Lys Asp Ile Thr Glu Glu Val Leu Lys Ser Ile Pro Ala Ser Glu Lys
            180                 185                 190

Ala Gln Glu Lys Lys
        195
```

(2) INFORMATION FOR SEQ ID NO: 3:

(i) SEQUENCE CHARACTERISTICS:
        (A) LENGTH: 22 amino acids
        (B) TYPE: amino acid
        (C) STRANDEDNESS: single
        (D) TOPOLOGY: linear     (ii) MOLECULE TYPE: peptide     (v) FRAGMENT TYPE: N-terminal     (vi) ORIGINAL SOURCE:
        (A) ORGANISM: Haemophilus influenzae     (xi) SEQUENCE DESCRIPTION: SEQ ID NO: 3:

```
Glu Glu Lys Ile Ala Phe Ile Asn Ala Gly Tyr Ile Phe Gln His His
 1               5                  10                  15

Pro Asp Arg Ala Val Lys
            20
```

(2) INFORMATION FOR SEQ ID NO: 4:

(i) SEQUENCE CHARACTERISTICS:

```
            (A) LENGTH: 29 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 4:

Ala Met Ala Thr Glu Asn Ile Ala Phe Ile Ser Gly Asp Tyr Leu Phe
1               5                   10                  15

Gln Asn His Pro Asp Arg Lys Met Val Ala Glu Lys Leu
            20                  25

(2) INFORMATION FOR SEQ ID NO: 5:

(i) SEQUENCE CHARACTERISTICS:
            (A) LENGTH: 26 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 5:

Ala Gly Lys Ile Ala Ile Val Asn Val Ser Ser Ile Phe Gln Gln Leu
1               5                   10                  15

Pro Ala Arg Glu Ala Val Ala Lys Gln Leu
            20                  25
```